Figure 1:
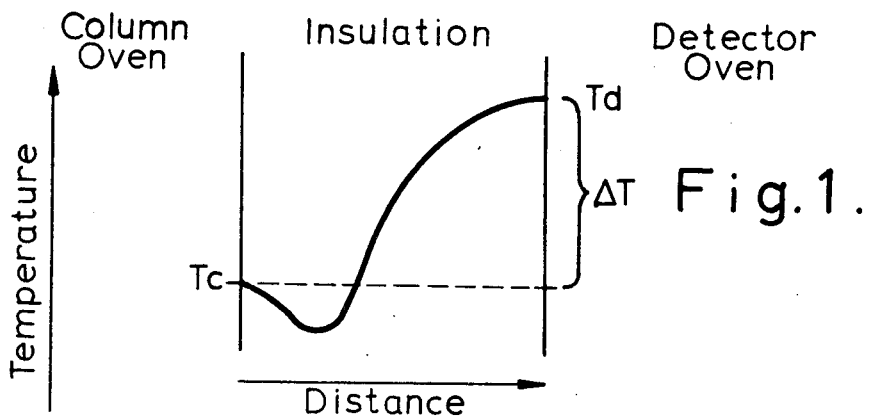

United States Patent [19]

Hunt

[11] 4,269,710
[45] * May 26, 1981

[54] CHROMATOGRAPHIC APPARATUS

[75] Inventor: Richard J. Hunt, Cambridge, England

[73] Assignee: Pye Limited, Cambridge, England

[*] Notice: The portion of the term of this patent subsequent to May 4, 1993, has been disclaimed.

[21] Appl. No.: 815,939

[22] Filed: Jul. 15, 1977

Related U.S. Application Data

[63] Continuation of Ser. No. 653,919, Jan. 30, 1976, abandoned, which is a continuation of Ser. No. 397,660, Sep. 17, 1973, Pat. No. 3,954,616.

[51] Int. Cl.³ ............................................. B01D 15/08
[52] U.S. Cl. ................................. 210/198.2; 55/197
[58] Field of Search .............. 210/198 C; 55/67, 197, 55/386, 267, 208; 23/232 C; 73/23.1

[56] References Cited

U.S. PATENT DOCUMENTS

| | | | |
|---|---|---|---|
| 3,057,183 | 10/1962 | Deford | 55/197 X |
| 3,498,027 | 3/1970 | Buchtel, Jr. | 55/197 |
| 3,578,785 | 5/1971 | Patterson | 55/197 X |
| 3,578,997 | 5/1971 | Felici | 55/267 X |
| 3,626,666 | 12/1971 | Drinkard | 55/67 |
| 3,719,084 | 3/1973 | Walker | 55/197 X |
| 3,954,616 | 5/1976 | Hunt | 210/198 C |

OTHER PUBLICATIONS

Gas Chromatography by Keulemans, Reinhold Pub. Co., New York, N. Y., 1960, pp. 60–64.

*Primary Examiner*—John Adee
*Attorney, Agent, or Firm*—Thomas A. Briody; Robert T. Mayer; Jack E. Haken

[57] ABSTRACT

Components eluted from a chromatographic column are conveyed to a detector through a conduit that is thermally conductive and in thermal contact with the detector so that negative thermal gradients are prevented when the detector is held at a temperature higher than that of the column.

5 Claims, 4 Drawing Figures

CHROMATOGRAPHIC APPARATUS

This is a continuation of application Ser. No. 653,919 filed Jan. 30, 1976, now abnd.; which is a cont. of Ser. No. 397,660, filed Sept. 17, 1978 now Patent 3,954,616.

This invention relates to chromatographic apparatus, and in particular to the temperature control thereof.

In chromatography it is normal for columns, detectors etc. to be maintained at various temperatures by means of ovens. The values of these temperatures vary depending on the application (i.e. the particular chromatographic separation being performed).

It is usual to attempt to keep detectors at a constant temperature, since their response may be affected by temperature changes. Among detectors whose response is critically affected by temperature is a katharometer. A flame ionisation detector, for example, is less affected.

Although the most reliable and repeatable separations are obtained by keeping the column temperature constant, it is sometimes desirable and necessary to programme the temperature of the column from a lower to a higher value. This is particularly useful in gas chromatography when mixtures with a wide boiling point range are being separated, or when materials of significantly different polarities are being separated on a polar column.

When temperature programming the column is enclosed in an oven whose temperature is varied. Typically the temperature may vary during the course of the separation process from 80° to 200° C.

The sample is normally transported from the column to the detector by being flushed by the mobile phase, which in the case of gas chromatography is a gas. During this transportation the sample diffuses within the mobile phase. Therefore to avoid loss of resolution in the detector due to spreading of the peaks, the internal volume of the pipework between the column and the detector should be kept as small as possible. From this point of view the chromatograph should be designed with the detector and column as close together as possible.

However when temperature programming, to put the ovens too close together would result in a change of heat transfer from the column oven to the detector oven causing the temperature of the detector oven to alter; an undesirable result, especially for katharometers and similar temperature sensitive detectors.

Also, when the column oven and detector oven are placed too close together, a high heat transfer rate through the insulation between them results in it not being possible to operate the column oven at low temperatures (e.g. 50°–60° C.) with the detector oven at moderately high temperatures (e.g. 200° C.) as is required in some temperature programming applications.

In view of the above, the usual arrangement is to place the ovens a reasonable distance apart and to attempt to isolate them thermally from each other. This arrangement leads to further difficulties in the temperature gradient along the tube which interconnects the column and the detector. Because of loss of heat to the surrounding insulation the temperature along the tube may exhibit a "cold spot" between the two ovens as shown in FIG. 1 of the accompanying drawings. This occurs even with a fairly large temperature difference $\Delta T$ between the column temperature Tc and the detector temperature Td. If the column oven is temperature programmed so that Tc approaches Td, the problem of the "cold spot" can become severe. The "cold spot" is undesirable in the chromatograph system. Firstly, as a result of column bleed, the gas leaving the column will be saturated with vapour formed from the stationary phase, and if the temperature of the gas drops, this vapour will condense on the wall of the tube. Then stationary phase can build up on the wall of the tube and partially block it. Secondly, the temperature drop in the interconnecting tube can cause the condensation of some constituents of the sample. This causes errors in the analysis and can also interfere with subsequent analyses. Furthermore, the magnitude of the temperature drop at the "cold spot" will vary as $\Delta T$ changes, e.g. during temperature programming.

In principle, the "cold spot" might be avoided by increasing $\Delta T$, by increasing the temperature Td of the detector oven. In practice this cannot be done to a great extent. Firstly, there is an effective upper limit on the operating temperature of the katharometer. The katharometer consists of a heated filament and a surrounding block with a fairly large temperature difference between them. The operation of the katharometer depends on the processes of thermal conduction from the filament by the gas, which are effected at high temperatures. The upper limit of the operating temperature of the filament is about 400° C. If the temperature Td were too high the filament could be only marginally hotter than the block. With the filament temperature at about 400° C., Td should be about 250° C. to achieve the maximum sensitivity of the detector. Secondly, some of the substances that may be investigated are thermolabile, and produce spurious peaks of the detector is run at too high a temperature. Thirdly, the column used may be glass, but the detector is probably made of stainless steel, which is more likely to react chemically with incoming materials. It is therefore advantageous to keep the detector temperature to a minimum.

Also, it might be possible to overcome the problem of the "cold spot" by the use of a separate oven for the interconnecting tube. However, this would involve the extra cost and inconvenience of additional heaters, controllers etc.

It is an object of the present invention to provide an interface between the column and the detector of a chromatographic apparatus which mitigates the above-mentioned difficulties.

According to the invention there is provided chromatographic apparatus including a chromatographic separation column, a detector responsive to components eluted from the column, means interconnecting the column and the detector for conveying the components from the column to the detector, a heating arrangement for maintaining the column and the detector at predetermined temperatures with the column temperature below the detector temperature, and a thermally conductive conduit in good thermal contact with the detector and surrounding the interconnecting means for at least part of the length thereof between the detector and the column, said thermally conductive conduit being adapted together with the heating arrangement so as to prevent the occurrence of a negative temperature gradient at any point along the interconnecting means.

The invention as defined above is applicable to gas chromatography, but is not necessarily limited thereto. It is envicaged that is is also applicable to other forms of column chromatography where the column and the detector must be kept at predetermined desired temperatures and where disadvantageous "cold spots" between the column and detector may otherwise occur.

According to the invention there is further provided gas chromatographic apparatus including an insulated column oven containing a chromatographic separation column, a separate insulated detector oven containing a detector responsive to the components eluted from the column and mounted on the column oven with only a small air gap between the two ovens, the two ovens being adapted to maintain the column and the detector at predetermined temperatures with the column temperature below the detector temperature, means adapted to provide thermal isolation in the air gap between the two ovens additional to that provided by the oven insulation, means interconnecting the column and the detector for conveying the components from the column to the detector, and a thermally conductive conduit in good thermal contact with the detector oven and surrounding the interconnecting means for at least part of the length thereof between the detector and the, column, said thermally conductive conduit being adapted to counteract the thermal isolation between the detector and the column to the extent that a negative temperature gradient is prevented from occurring at any point along the interconnecting means.

Figure 4:
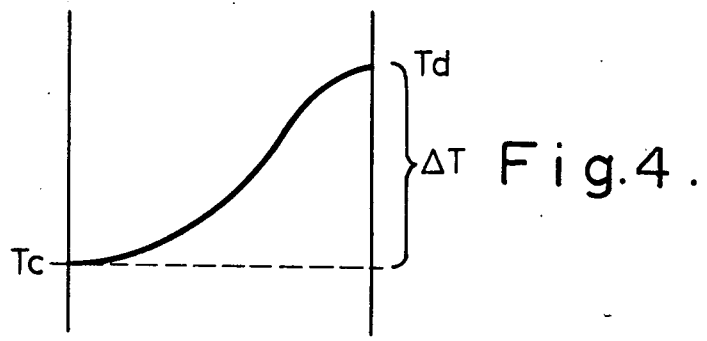
Figure 3:
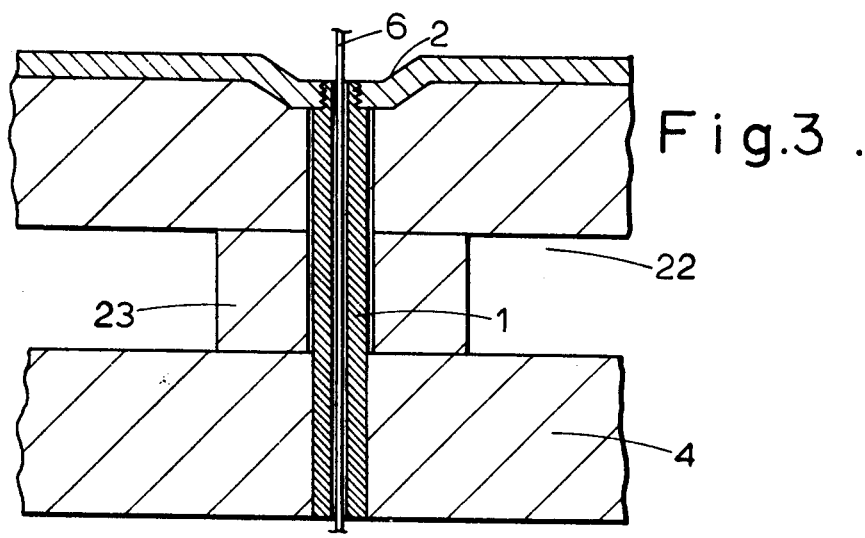
Figure 2:
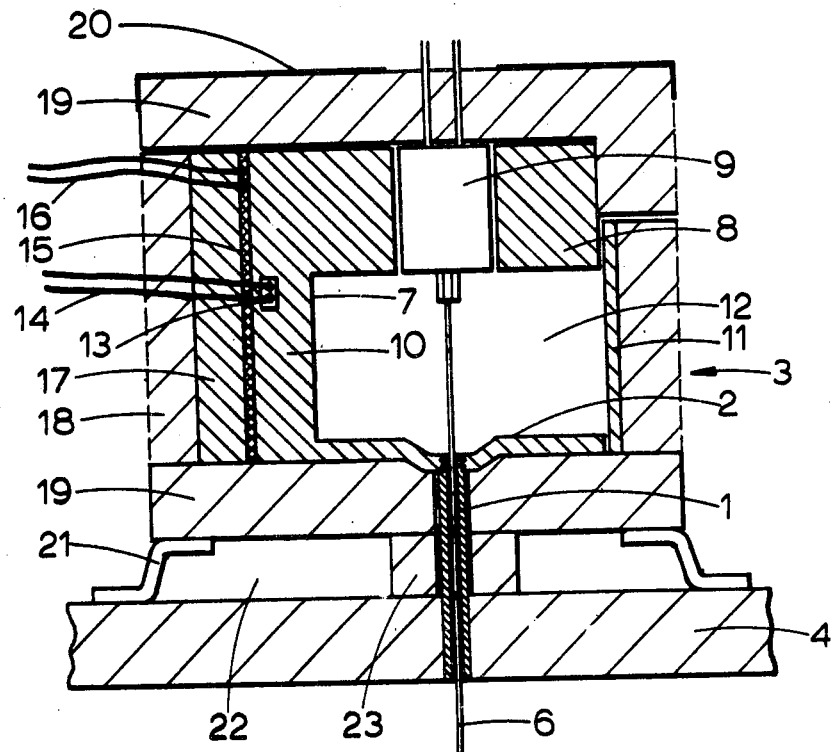
Figure 2:
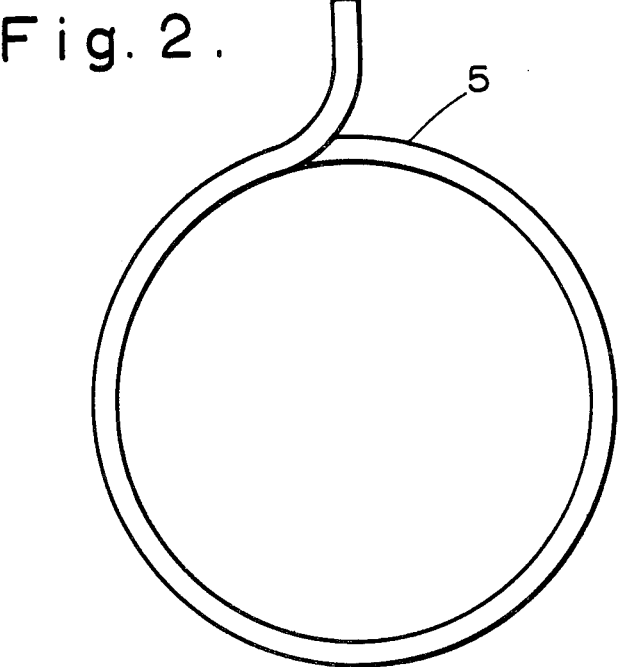

In the accompanying drawings:

FIG. 1 is a graph showing a typical prior art temperature gradient along the interconnecting tube between the column and detector;

FIG. 2 schematically shows part of a gas chromatograph,

FIG. 3 schematically shows part of FIG. 2 on an enlarged scale, and,

FIG. 4 is a graph showing a typical temperature gradient along the interconnecting tube between the column and detector of the gas chromatograph shown in FIGS. 2 and 3.

An example of the invention will now be described.

Referring now to FIGS. 2 and 3, an interface conduit tube 1 of thermally conductive material, in this case aluminium bronze, is firmly screwed into and is in good thermal contact with an conductive base wall 2 of a detector oven 3. The other end of the tube 1 passes through the insulation 4 of a column oven containing a separation column 5. The internal diameter of the tube 1 is such that atube 6, carrying gas from the column to the detector, can easily pass through it. More than one interconnecting tube 6 will often be used, for example if more than one column is used, in which case a corresponding number of interface tubes 1 will be used. In this embodiment the gas transfer tubes 6 may be of 1/16" (1.58 mm) outer diameter stainless steel, alternatively they could be glass-lined steel tubing. The outer diameter of the interface tube 1 is chosen such that heat will pass along the tube 1 at a desired rate with a desired temperature gradient. These factors also depend on the dimensions and thermal properties of the oven walls into which the tube is screwed. The thickness of the detector oven wall 2 at the base of the oven may be 5 millimeters and the outer diameter of the tube 1 may be 12 millimeters.

The detector oven 3 is formed from a block 7 of thermally conductive material, e.g. an aluminium alloy. Most of the mass of the block is in the upper part 8 which surrounds a detector such as a katharometer 9 and maintains it at an even temperature. Below this part 8, the side walls of the oven, two of these walls 10, 11 being shown in FIG. 2, enclose an air-space 12 and maintain it at substantially the same temperature as the detector. This air space allows ancillary apparatus which may be required, such as gas-splitters (not illustrated), to be conveniently maintained at the same temperature as the main detector 9. The upper part 8 of the block may include two additional spaces (not shown) disposed in a line parallel to the walls 10, 11 on either side of the space for the katharometer 9. These spaces may each contain a flare ionisation detector or other instrument to which gas may be fed by means of the gas splitter. The side wall 11 is a hinged door which provides convenient access to such ancillary apparatus and to the bases of the detectors. In a hole drilled in the side wall 10 there is a temperature detector 13 (e.g. a resistance thermometer), with leads 14 which enables the heating of the oven itself to be controlled. In a similar hole (not shown) there is a thermocouple or the like which operates a cut-out of the oven heating at about 400° C. to protect the katharometer filament. On the outside of the side wall 10 there is a heater plate 15 (with leads 16) which heats the oven. Outside the heater plate is a backplate 17 whose shape, size and thermal capacity are chosen in relation to the conductive block 7 and the position of the temperature detector 13 such that there is not an undue rise in the temperature in the block after the temperature detector and controller have caused the heating current to be switched off. These parts of the oven are surrounded by insulation. In certain regions, insulation such as ceramic fibre 18 may be used; in other regions where some structural strength is desirable insulating material such as asbestos/cement board 19 is used. The oven is surrounded by a metal plate 20 to form keys for the detectors.

The oven is supported by steel brackets 21 which in turn are supported on the top of the column oven insulation, thus providing an air gap 22 between the column and detector ovens. The interface tube 1 is surrounded by insulation 23 where it passes through this gap. A fan (not shown) is provided which circulates air in the gap 22 and thus provides a degree of thermal isolation between the column and detector ovens additional to that provided by the oven insulation.

Thus the heat transfer from the detector oven to the column oven is small; and although the heat produced by the column oven changes during the temperature programming this has an insignificant effect on the detector oven temperature. The positive air-cooling between the ovens is only possible because the heat loss from the interconnecting insulation 23 is made up by the heat flowing along the interface tube 1 from the detector oven. The air-cooling means that the ovens can be kept close together without affecting each other. As explained above, this reduces the spreading of the peaks due to diffusion in the mobile phase.

A typical temperature gradient along the gas transfer tube 6 is shown in FIG. 4. The interface tube 1 prevents a negative temperature coefficient from occurring at any point along the gas tube 6 between the two ovens with a temperature difference $\Delta T$ of as little as 15° C. between the column oven and the detector oven, both being at about 200° C.

The heat transfer pattern can be altered by changing the geometry of the components and by changing the materials. For example, the thickness of the base wall 2 of the detector oven affects the heat flow. The outer diameter of interface tube 1 may be varied along its length to obtain a particular desired temperature gradient. However, special profiles of the tube 1 are not normally necessary to provide a heat transfer of the desired kind.

Modifications of the form of the interface tube are possible. Instead of the interface tube 1 being screwed into the base wall 2 of the detector oven as described above, the interface tube may terminate in an outwardly extending flange; in this case the flange can be secured to the underside of the oven wall 2 by screws, or otherwise the interface tube may pass through the hole in the oven wall 2 with the flange resting on top of the wall 2 and secured thereto by screws. As another possibility the interface tube may be formed as an integral part of the base of the detector oven, or may be an enlarged portion of the gas-carrying interconnecting tube itself. If the detector and method of heating the detector are such that the detector is not contained in an oven, the interface conduit may be attached to and in thermal contact with the detector, or may be formed as an integral part of the detector.

What we claim is:

1. Chromatographic apparatus comprising:
    a chromatographic separation column;
    means for maintaining the temperature of said column at a first predetermined temperature;
    a detector responsive to components eluted from said column;
    conduit means which function to convey components from said column to said detector; and
    means for heating said conduit means which function to conduct and retain heat from said detector along said conduit and prevent the formation of negative temperature gradients along said conduit means.

2. Chromatographic apparatus as defined in claim 1, wherein said conduit means comprise a metal tube.

3. Chromatographic apparatus as defined in claim 2 and further comprising detector heating means in thermal contact with said detector which function to maintain said detector at a higher predetermined temperature than said column.

4. Chromatographic apparatus as defined in claim 3, wherein said detector heating means has a thermally conductive wall and said metal tube is in thermal contact therewith.

5. Chromatographic apparatus as defined in claim 4, wherein said means for maintaining the temperature of said column and said detector heating means are spaced from each other to define an air gap which is traversed by said metal tube and said means for heating said conduit include thermal insulation surrounding said metal tube at least over the portion thereof traversing said air gap.

* * * * *